United States Patent [19]

Engel et al.

[11] 4,170,636

[45] Oct. 9, 1979

[54] COMPOSITION AND METHOD FOR INHIBITING PLAQUE FORMATION

[75] Inventors: Michael R. Engel, White Bear Lake; Robert W. H. Chang, Shoreview; Linda L. LaFleur, Oakdale, all of Minn.

[73] Assignee: Minnesota Mining and Manufacturing Company, St. Paul, Minn.

[21] Appl. No.: 865,680

[22] Filed: Dec. 29, 1977

[51] Int. Cl.$^2$ .............................................. A61K 7/18
[52] U.S. Cl. ...................................................... 424/52
[58] Field of Search ................................... 424/48–58

[56] References Cited

U.S. PATENT DOCUMENTS

| | | | |
|---|---|---|---|
| 2,567,611 | 9/1951 | Diesslin et al. | 260/465.7 |
| 2,759,019 | 8/1956 | Brown et al. | 260/556 |
| 2,809,990 | 10/1957 | Brown | 260/564 |
| 2,829,086 | 4/1958 | Kirschonbauer | 424/52 |
| 2,955,985 | 10/1960 | Kuna | 424/52 |
| 3,346,612 | 10/1967 | Hansen | 260/456 |
| 3,535,421 | 10/1970 | Briner et al. | 424/52 |
| 3,584,116 | 6/1971 | Francis et al. | 424/52 |

OTHER PUBLICATIONS

March Advanced Organic Chemistry : Reactions, Mechanisms and Structures, pp. 324, 368, McGraw-Hill, (1968).

*Primary Examiner*—Shep K. Rose
*Attorney, Agent, or Firm*—Cruzan Alexander; Donald M. Sell; James V. Lilly

[57] ABSTRACT

A dentifrice composition is provided which contains a compound having the formula $(R_f)_m YX$ wherein $R_f$ is a fluoroaliphatic radical having from about 4 to 16 carbon atoms; Y is a calcium-complexing moiety; X is a terminal group which does not interfere with the complexing ability of said calcium-complexing moiety; and m is an integer of at least one. A method of inhibiting plaque formation in an oral environment is also provided.

16 Claims, No Drawings

COMPOSITION AND METHOD FOR INHIBITING PLAQUE FORMATION

BACKGROUND OF THE INVENTION

1. Field of the Invention

This invention relates to compositions and methods useful in inhibiting the growth of cariogenic bacteria and the formation of plaque on teeth in an oral environment.

2. Prior Art

The prevention of the formation of dental plaque is a highly desired result. Dental plaque results when cariogenic bacteria (e.g., *Streptococcus Mutans*), collect in colonies on the teeth and form a tenacious deposit thereon. The presence of the bacteria and the deposits is extremely detrimental to the health of the teeth. Thus, if the cariogenic bacteria and the plaque formation are not checked they may result in infected gingival tissue, the formation of dental caries and peridontal disease. In extreme cases they may ultimately result in the loss of the teeth.

To overcome these problems many attempts have been made to control each. For example, fluoride solutions or gels have been used. Treatment with these materials is typically performed in a dental office at periodic, but not frequent intervals. The primary objective of such treatments is to render the tooth enamel more resistant to the acid action caused by plaque. Such treatments do not, however, result in plaque control for an extended period since plaque reestablishes itself on the teeth shortly after ingestion of food.

Even when the frequency of application of such solutions and gels is increased only partial control has been shown. For example, studies wherein a fluoride-containing solution (1% fluoride concentration) was applied four to five times in the course of a year have demonstrated that this technique had only limited success due to the rapid reestablishment of plaque in the oral cavity. Moreover, the daily application of a fluoride gel by means of a customfitted polyvinyl mouthpiece for a period of 21 months also showed no substantial change in plaque formation among treated and untreated patients. See "Clinical Anticaries Effect of a Repeated Sodium Fluoride Application by Mouthpiece", Journal of the American Dental Association, V. 75, No. 3, September, 1967, pp. 638-644.

Other attempts at inhibiting the formation of plaque have also been made. Thus British Pat. No. 1,319,247 describes dental compositions which comprise a dental vehicle and a zinc, copper or zirconium complex of a fluorinated beta-diketone. These compounds are said to reduce the solubility of tooth enamel in the acids produced by bacteria in the mouth.

SUMMARY OF THE INVENTION

The present invention provides a dentifrice composition, substantially free from polyvalent metal ions (e.g., $Ca^{++}$, $Mg^{++}$, etc.), which contains a fluorochemical material having the formula $(R_f)_m YX$. In this formula $R_f$ is a fluoroaliphatic radical having from about 4 to 16 carbon atoms;

Y is a calcium-complexing moiety which has a formation constant in the range of about 0.5 to 8, wherein said calcium complexing moiety forms a complex structure with calcium, which structure contains up to about 20 atoms in its backbone;

X is a terminal group which does not interfere with the ability of said complexing moiety to form said complex structure with calcium; and m is an integer of at least one.

Preferably compositions of the present invention comprise at least about 0.05% by weight, and most preferably from about 0.1% to 1% by weight, of the fluorochemical compound.

In another embodiment of the present invention there is provided a method for inhibiting plaque formation which comprises contacting teeth with an effective amount of the above-described dentifrice composition.

As it is used throughout the specification, the term "dentifrice" refers to compositions for topical application to teeth. Representative of such compositions are liquids (e.g., mouthwashes and rinses, etc.) and toothpastes (in the form of gels, powders or pastes) etc.

DETAILED DESCRIPTION OF THE INVENTION

The dentifrice compositions of the invention may be applied to teeth by a variety of techniques including, for example, painting or brushing, spraying, bathing and rinsing. Other means of application are also possible and will be obvious to those skilled in the art as a result of this disclosure.

Fluorochemical materials, useful in the invention have the formula set forth above. In this formula $R_f$ is a fluorinated, saturated, usually monovalent, aliphatic radical. The $R_f$ radicals are stable, inert, nonpolar moieties which can be both olephobic and hydrophobic. They can be straight chain or branched chain radicals. Additionally, if the radicals are sufficiently large, they may be cyclic or combinations of cyclic and branched and straight chain. (e.g., alkylcycloaliphatic radicals). The skeletal chain of the $R_f$ radical can include catenary oxygen and/or trivalent nitrogen hetero atoms bonded only to carbon atoms. Such hetero atoms provide stable linkages between fluorocarbon groups and do not interfere with the inert character of the radical.

$R_f$ has from about 4 to 16 carbon atoms. Preferably it has from about 6 to 12 carbon atoms. Additionally the $R_f$ radical is preferably fully or substantially fully fluorinated. Thus the preferred $R_f$ radicals are perfluoroalkyl groups (e.g., $C_nF_{2n+1}-$). Additionally the terminal portion of the $R_f$ group preferably contains a $-CF_3$ group, and most preferably the terminal portion also has at least three fully fluorinated carbon atoms, (e.g., $CF_3CF_2CF_2-$).

Generally the $R_f$ radical contains about 40-80 percent by weight, and preferably 50-80 percent by weight, fluorine, As a result, the corresponding fluorochemicals contain from about 4 to 70 percent by weight fluorine.

Complexing moieties (Y) useful in the present invention may be mono- or polydentate. The fluorochemicals form complex (e.g., chelate) structures with calcium through the Y group. These complex structures may contain up to about 10 atoms in their backbone. Preferably they contain from about 5 to 6 members therein. Additionally, the calcium complexing moieties have a formation constant within a defined range. This constant is expressed in terms of $\log_{10}K$. Useful calcium complexing moieties have a formation constant in the range of about 0.5 to 8. Values of more than 8 indicate very strong calcium chelators. Such chelators are undesirable because they decalcify the tooth (i.e., withdraw the calcium from the tooth) thereby weakening its resistance to disease and wear.

The formation constant is based upon a complex formed between the fluorochemical and an organic ligand. The value is determined at about 25° C. and an ionic strength approaching 0 from the following:

$$M + L \rightleftarrows ML$$
$$K = \frac{[ML]}{[M][L]}$$

In these formulae M represents the complexing agent; L represents the organic ligand; and ML represents the complex. The bracketed symbols indicate concentration of the indicated material at equilibrium.

The chelate structure formed between the fluorochemical and calcium of the tooth may be represented by the general structure:

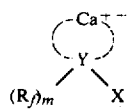  I.

wherein $R_f$, Y, X and m are as described above. For purposes of discussion the Y group is hereinafter sometimes represented by the formula —A—Z—A—. Thus structure I may also be represented by

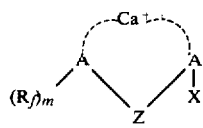  II.

wherein each $R_f$, $R^1$ and m are as described above; each A is an electron donating moiety that may be the same or different and is selected from (i) hetero atoms selected from oxygen, nitrogen and sulfur, provided that when A is nitrogen it is either a primary or secondary nitrogen; and (ii) groups which contain the above-described hetero atoms; and Z is a connecting group which does not interfere with the formation of the chelate structure.

Representative examples of useful A groups are ketone groups, hydroxyl groups, carboxyl groups, amino groups, sulfhydryl groups, thionogroups, thiologroups, mercapto groups, etc. Fluorochemicals which contain more than one of these A groups are also useful (e.g., hydroxy-carboxylic, sulfhydryl-carboxylic, sulfhydryl-thiolo, sulfhydryl thiono, amino-mercapto, etc.).

Representative examples of useful Z groups include alkylene radicals containing from about 1 to 20 carbon atoms; and arylene radicals of from about 5 to 20 carbons. Hetero atoms (e.g., nitrogen, oxygen and sulfur) may appear in the Z groups. However they must not interfere with chelation of the calcium.

Still other Y groups useful in the present invention comprise quaternary nitrogen groups. These groups may be represented by the formula

wherein $R^4$ and $R^5$ are methyl and $R^6$ is —(CH$_2$)$_b$W wherein b is an integer of from about 1 to 6 and W is selected from the group consisting of hydrogen, hydroxyl and

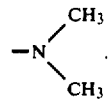

Typically the quaternary nitrogen moieties are associated with an anionic moiety. Representative examples of such anoinic moieties are —H$_2$PO$_4$⊖ and —NO$_3$⊖. Still other anionic moieties are also useful as will be understood by those skilled in the art.

X groups useful in the fluorochemical materials do not interfere with the ability of the Y group to form complex structures with calcium. A variety of groups may function as the X group. Representative examples of such groups are hetero atoms such as hydrogen and alkali metals (e.g., potassium and sodium), alkyl radicals, especially those containing from about 1-4 carbons, carboxyl and sulfonate radicals, aryl radicals (e.g., those containing from about 5 to 6 carbon atoms), ammonium radicals and heteroatoms.

In an alternative embodiment of the present invention the fluorochemical material may be represented by the formula $(R_f)_mQYX$ wherein $R_f$, Y, X and m are each as described above and wherein Q is a polyvalent (i.e., at least divalent) linking group through which $R_f$ and Y are bonded together. Representative examples of useful Q groups include polyvalent aliphatic; polyvalent aromatic, oxy, thio, carbonyl, sulfone, sulfoxy, imino, and combinations thereof such as oxyalkylene, iminoalkylene, iminoarylene, sulfonamideo, carbonamido, sulfonamidoalkylene, carbonamidoalkylene, urethane, etc.

Representative examples of polyvalent aliphatic Q groups include —CH$_2$—CH$_2$—, and —CH$_2$C(CH$_2$O)$_3$—. Representative examples of polyvalent aromatic Q groups include

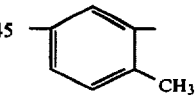

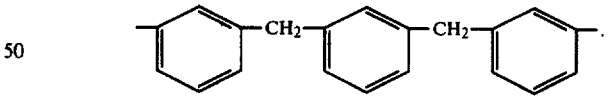

Representative examples of imino Q groups include —NH— and —N(C$_2$H$_5$)—. Representative of suitable urethane Q groups include —CH$_2$CH$_2$OCONH— and

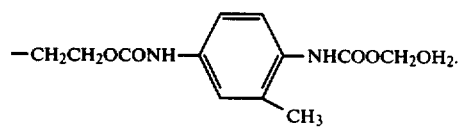

Specific examples of fluorochemical materials which conform to the formulae set forth previously are illustrated in Table 1. The specific formula and the portion of each material attributable to each element of the generic formula are given.

TABLE 1

| SPECIFIC FORMULA | $R_f$ | Q | Y | X |
|---|---|---|---|---|
| 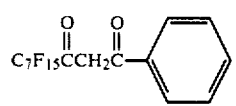 | $C_7F_{15}-$ | — |  | 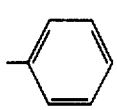 |
| 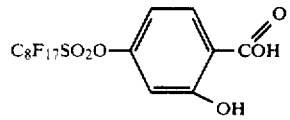 | $C_8F_{17}-$ | $-SO_2-$ | 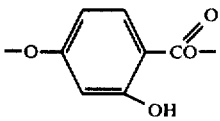 | $-H$ |
| $C_8F_{17}SO_2NCH_2COH$<br>$\quad\quad\quad\quad\ \|$<br>$\quad\quad\quad\quad C_2H_5$ (with =O on C) | $C_8F_{17}-$ | $-SO_2-$ | $-NCH_2CO-$<br>$\ \|$<br>$C_2H_5$ (C=O) | $-H$ |
| $[C_8F_{17}SO_2NHC_3H_6-\overset{\oplus}{N}-(CH_3)_2]NH_3^{\ominus}$<br>$\quad\quad\quad\quad\quad\quad\quad\ \|$<br>$\quad\quad\quad\quad\quad\quad\quad C_2H_4OH$ | $C_8F_{17}-$ | $-SO_2-$ | $NHC_3H_6\overset{\oplus}{N}(CH_3)_2-$<br>$\ \|$<br>$C_2H_4OH$ | $-NO_3^{\ominus}$ |
| $[C_8F_{17}SO_2NHC_6-\overset{\oplus}{N}(CH_3)_2]H_2PO_4^{\ominus}$<br>$\quad\quad\quad\quad\quad\ \|$<br>$\quad\quad\quad\quad\ C_2H_4OH$ | $C_8F_{17}-$ | $-SO_2-$ | $NHC_3H_6-\overset{\oplus}{N}(CH_3)_2$<br>$\ \|$<br>$C_2H_4OH$ | $-H_2PO_4^{\ominus}$ |
| | $C_8F_{17}-$ | $-SO_2-$ | $-N(CH_2)_{10}-\overset{O}{\overset{\|}{C}}-O$<br>$\ \|$<br>$CH_3$ | $-H$ |
| $C_8F_{17}SO_2NCH_2COK$<br>$\quad\quad\quad\quad\ \|\ \ \ \|$<br>$\quad\quad\ C_2H_5\ \ O$ | $C_8F_{17}-$ | $-SO_2-$ | $-NCH_2CO-$<br>$\ \|\ \ \ \|$<br>$C_2H_5\ \ O$ | $-K$ |
| $CF_2H\quad\quad\quad OH$<br>$\ \|\quad\quad\quad\quad \|$<br>$CF_3CFC_{13}F_{26}CONHCH_2CHCH_2NH\ \rceil$<br>$\quad\quad\quad\quad\quad\quad HOH_2CHOHCH_2C\ \rfloor$ | $CF_3CFC_{13}F_{26}-$ | | $-CONHCH_2CH(OH)CH_2NH-$ | $-CH_2CHOHCH_2OH$ |
| $C_8F_{17}SO_2N(C_2H_5)CH_2CO_2H(HOCH_2CH_2)_3N$ | $C_8F_{17}$ | $SO_2-$ | $-N(C_2H_5)CH_2CO_2-$ | $-H(HOCH_2CH_2)_3N$ |

The foregoing fluorochemical materials and the methods of their preparation are known. Thus, the preparation of

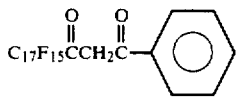

may be carried out by taking the appropriate fluorocarbon carboxylic acid (i.e., $C_{17}F_{15}COOH$), alkylating that acid with the appropriate diazo compound (i.e., $CH_2N_2$) to form the ester and then treating the ester with the appropriate ketone

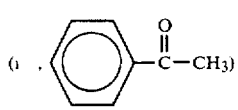

to give the diketone. The fluorochemical carboxcyclic acid is known from U.S. Pat. No. 2,567,011 (issued Sept. 4, 1951). The various reactions to convert the carboxcyclic acid are known from March, Advanced Organic Chemistry: Reactions, Mechanisms, and Structures, pp. 324,368, McGraw-Hill (1968)

The preparation of

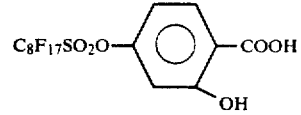

is described in U.S. Pat. No. 3,346,612 (issued Oct. 10, 1967).

The preparation of $C_8F_{17}SO_2NCH_2COOH;$
$\quad\quad\quad\ \|$
$\quad\quad\ C_2H_5$ $C_8F_{17}SO_2N(CH_2)_{10}COOH;\ C_8F_{17}SO_2NCH_2COOK$ and
$\quad\quad\quad\ \|\quad\quad\quad\quad\quad\quad\quad\quad\quad\quad\quad\ \|$
$\quad\quad\ CH_3\quad\quad\quad\quad\quad\quad\quad\quad\quad\quad\ C_2H_5$ $C_8F_{17}SO_2NCH_2CO_2H(HOCH_2CH_2)_3N$
$\quad\quad\quad\ \|$
$\quad\quad\ C_2H_5$ is described in U.S. Pat. No. 2,809,990 (issued Oct. 15, 1957).

The preparation of $[C_8F_{17}SO_2NHC_3H_6-\overset{\oplus}{N}H(CH_3)_2]NO_3^{\ominus}$ and $[C_8F_{17}SO_2NHC_3H_6-\overset{\oplus}{N}(CH_3)_2]H_2PO_4^{\ominus}$
$\quad\quad\quad\quad\quad\quad\quad\ \|$
$\quad\quad\quad\quad\quad\quad C_2H_4OH$ is described in U.S. Pat. No. 2,759,019 (issued Aug. 14, 1956) with the exception that different but known quaternizing agents are used.

A variety of other ingredients may be added to the compositions of the present invention. Thus, for example, prophylactic agents may be included. Moreover, polishing agents, surfactants, flavoring and sweetening agents, thickening agents and humectants may be included using techniques which are known to the art.

Such other ingredients must be substantially free of polyvalent metal ions (e.g., $Ca^{++}$, $Mg^{++}$ etc.). The presence of such ions prevents the compositions of the invention from exhibiting the desired control over cariogenic bacteria and plaque formation. While the reason for this is not fully understood, it is believed that these ions interact with the fluorochemical materials before application of the composition to teeth thereby preventing them from interacting with the calcium of the teeth. Thus while these ingredients may contain a minor amount of polyvalent metal ions, the total amount of such ions present must not prevent the fluorochemical materials from interacting with the teeth. Preferably these other ingredients are completely free from any polyvalent metal ions.

Representative prophylatic agents include supplemental caries-preventing materials such as sodium fluoride, stannous fluoride, potassium fluoride, hexylamine hydrofluoride, myristylamine hydrofluoride, betaine fluoride, glycine potassium fluoride, etc. A particularly preferred fluoride is sodium fluoride. Typically these prophylactic agents are present in sufficient concentration so as to provide an available fluoride ion concentration of up to about 2% by weight, and preferably in the range of about 0.5–2% by weight, of the dentifrice composition.

Suitable polishing agents include, for example, water-impervious crosslinked thermosetting resins such as the condensation products of melamine and urea with formaldehyde. Other suitable polishing agents will be obvious to those skilled in the art as a result of this disclosure. Preferably the polishing agent is not so abrasive so as to scratch or unduly abrade the tooth surface or the dentin. Rather it only cleans the tooth surface. The polishing agents may comprise up to about 95% by weight of the dentifrice composition.

Surfactants may also be employed in compositions of the invention. Suitable surfactants include, for example, detergent materials and are preferably nonionic. Representative examples of useful surfactants include lauric monoethanolamide, lauric-myristic monoethanolamide, ricinoleic alkanolamides, fatty acid alkanolamides (e.g., coconut diethanolamide), lauryl dimethyl amine oxide, glycerol monolaurate, glycerol monostearate, pentaerythritol monooleate, sorbitan monooleate, ethoxylated castor oil, nonyl phenol ethoxolate, etc. The surfactants typically comprise up to about 5% by weight of the dentifrice composition.

Suitable flavoring and sweetening agents which may be employed in compositions of the invention include, for example, the oils of wintergreen, peppermint, spearmint, sassafras and anise. Additionally small amounts of sweetening agents such as saccharin, dextrose, levulose, etc. may also be added to such compositions. These flavoring and sweetening agents may comprise up to about 5% by weight of the dentifrice composition.

Suitable gelling or thickening agents which may be employed in compositions of the present invention include, for example, natural gums such as gum karaya, gum arabic, and gum arabic, and gum tragacanth; and finely divided silica. Such thickening agents may comprise up to about 5% by weight of the dentifrice composition.

Suitable humectants which may be employed in compositions of the invention include glycerine, sorbitol, and other polyhydric alcohols. The humectants may comprise up to about 35% by weight of the dentifrice composition.

The effectiveness of the present invention in inhibiting the growth of plaque was demonstrated by both in vitro and in vivo tests. These tests are described more fully in the following examples.

EXAMPLE 1

In vitro tests were performed on plaque-free bovine teeth. The teeth were dipped into a composition of the invention for 30 minutes and then air dried for 30 minutes. Untreated teeth were used as controls. The treated and untreated teeth were then suspended in tubes of a test media comprising 18 milliliters of actinomyces broth, 2 milliliters of a 20% aqueous sucrose solution, and 0.2 milliliters of a 24 hour viable culture of *Streptococcus mutans*. The teeth and test tubes were incubated at 37° C. for 24 hours, after which the teeth were transferred to new test tubes of fresh test media and again incubated at 37° C. for 24 hours. The procedure was repeated for three days or until attachment of plaque to the control teeth was noted.

The compositions used to treat the teeth comprised 1% by weight fluorochemical and 99% by weight deionized water. Compositions containing the following fluorochemicals, each of which had a formation constant in the range of about 0.5 to 8, were found to prevent the formation of plaque in this test:

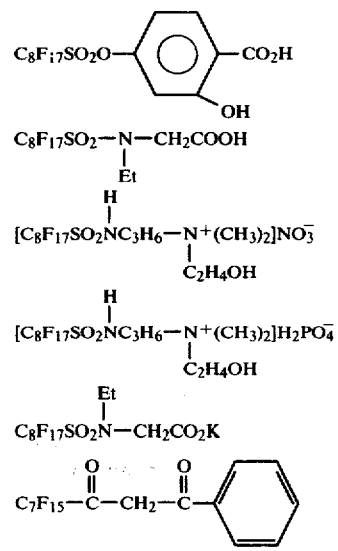

EXAMPLE 2

In vivo tests were performed on Rhesus Monkeys. Each monkey received a complete dental prophylaxis wherein their teeth were ultrasonically cleaned and then polished using a soft rubber prophylaxis cup and standard pumice-filled prophylaxis paste. The test compounds were applied to the upper central and medial incisors of each monkey by brushing about 0.5 cc of a solution of the fluorochemical material in deionized water and allowing the teeth to air dry for about 30 seconds. Various concentrations of the fluorochemicals were employed in the solutions tested. The lower central and medial incisors of the monkeys served as control teeth. Except for the initial dental prophylaxis, the control teeth received no treatment during the tests. The teeth were observed for up to 14 days to determine the effect of the treatment upon the formation of plaque.

The monkeys were fed twice a day with a diet which encouraged plaque formation. Each feeding consisted of about 135 grams of Purina ® New World Monkey Chow ® which had been softened with 200 grams distilled water and to which had been added 118 grams of sugar. The Monkey Chow ® is commercially available from Ralston Purina Co. It has a guaranteed analysis of

| Crude protein not less than | 25.0% |
|---|---|
| Crude fat not less than | 5.0% |
| Crude fiber not more than | 3.5% |
| Added minerals not more than | 3.0% |
| Ash not more than | 6.0% |

The ingredients in the Monkey Chow ® were ground yellow corn, soybean meal, ground wheat, corn gluten meal, dried skimmed milk, animal fat preserved with BHA, sucrose, brewers' dried yeast, salt, dehydrated alfalfa meal, vitamin $B_{12}$ supplement, riboflavin supplement, calcium pantothenate, niacin, choline chloride, menadione sodium bisulfite (source of vitamin K activity), folic acid, pyridoxine hydrochloride, thiamin, ascorbic acid, vitamin A supplement, D activated animal sterol (source of vitamin $D_3$), vitamin E supplement, iron oxide, iron sulfate, manganese sulfate, calcium iodate, calcium carbonate, dicalcium phosphate, manganous oxide, copper oxide, cobalt carbonate, zinc oxide.

The effectiveness of plaque inhibition in this test was measured by means of a plaque index number. The plaque index was determined by applying Erythrosine B dye (further identified as FD&C Red dye #3, Color Index No. 45430) to the teeth. This dye stains plaque but not tooth enamel. The stained plaque was visually observed and assigned a number using the following scale.

| PLAQUE SCALE | |
|---|---|
| 0 | No plaque |
| 0.25 | Light plaque covering about ¼ of tooth surface |
| 0.5 | Light plaque covering about ½ of tooth surface |
| 0.75 | Light plaque covering above ¾ of tooth surface |
| 1.0 | Light plaque covering entire tooth surface. |
| 1.25 | Heavy plaque on ¼ of tooth surface, light plaque on remainder. |
| 1.50 | Heavy plaque on ½ of tooth surface, light plaque on remainder. |
| 1.75 | Heavy plaque on ¾ of tooth surface, light plaque on remainder. |
| 2.0 | Heavy plaque on entire tooth surface. |

The teeth were stained and observed visually periodically throughout the test. The ratings were averaged to form the plaque index. The results of these tests are set forth in Table 2. The fluorochemical materials employed were

A.

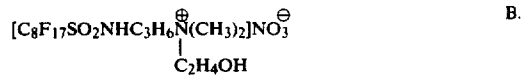

B.

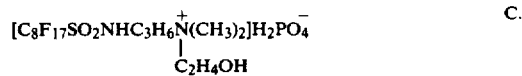

C.

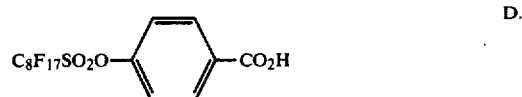

D.

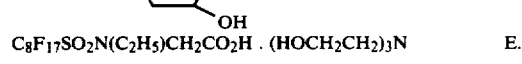

E.

TABLE 2

| MONKEY | FLUOROCHEMICAL MATERIAL | APPLICATION METHOD | CONCENTRATION (Wt. %) | TEST LENGTH (Days) | PLAQUE INDEX TREATED TEETH | PLAQUE INDEX CONTROL TEETH |
|---|---|---|---|---|---|---|
| 1 | A | * | 2 | 14 | 0.25 | 1.687 |
| 2 | A | * | 1 | 14 | 0.125 | 1.375 |
| 3 | A | * | 0.5 | 14 | 0.125 | 3.437 |
| 4 | A | * | 0.25 | 14 | 0.50 | 1.375 |
| 5 | A | * | 0.125 | 14 | 0.666 | 2.50 |
| 1 | A | ** | 1 | 13 | 0.35 | 1.15 |
| 1 | A | ** | 1 | 8 | 0.333 | 1.75 |
| 6 | A | ** | 1 | 10 | 0.375 | 1.31 |
| 7 | A | ** | 1 | 10 | 0.187 | 1.56 |
| 8 | A | ** | 1 | 12 | 0.4 | 1.35 |
| 9 | A | ** | 1 | 8 | 0.166 | 2.0 |
| 1 | B | * | 1 | 14 | 0.70 | 1.60 |
| 6 | B | * | 1 | 8 | 0.5 | 2.0 |
| 7 | B | * | 1 | 8 | 0.208 | 1.50 |
| 10 | B | * | 1 | 10 | 0.125 | 1.3125 |
| 2 | C | * | 1 | 10 | 0 | 1.125 |
| 2 | C | * | 1 | 14 | 0.1 | 1.35 |
| 10 | C | * | 1 | 14 | 0.416 | 1.58 |
| 4 | D | * | 1 | 14 | 1.083 | 1.875 |
| 11 | D | * | 1 | 13 | 0.11 | 1.39 |

TABLE 2-continued

| MONKEY | FLUOROCHEMICAL MATERIAL | APPLICATION METHOD | CONCENTRATION (Wt. %) | TEST LENGTH (Days) | PLAQUE INDEX TREATED TEETH | PLAQUE INDEX CONTROL TEETH |
|---|---|---|---|---|---|---|
| 12 | E | * | 1 | 10 | 0 | 1.00 |

Application Techniques
*Daily brushing with fluorochemical solution
**Daily rinsing with fluorochemical solution

What is claimed is:

1. A dentifrice composition comprising at least one ingredient selected from the group consisting of caries prophylatic agents, polishing agents, surfactants, flavoring agents, sweetening agents, thickening agents and humectants, said ingredients being substantially free from polyvalent metal ions, and at least 0.05% by weight of a fluorochemical compound selected from

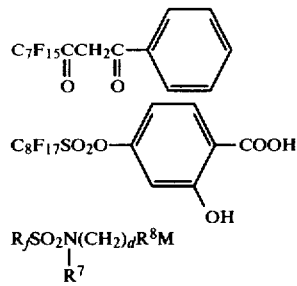

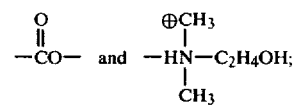

wherein $R_f$ is a fluorinated, saturated, aliphatic radical having from about 4 to 16 carbon atoms;

$R^7$ is selected from hydrogen, methyl and ethyl;

$R^8$ is selected from $$-\overset{O}{\underset{\|}{C}}O- \quad \text{and} \quad -\overset{\oplus}{\underset{|}{\underset{CH_3}{N}}}-C_2H_4OH;$$

M is selected from hydrogen, sodium, potassium, $-HN(CH_2CH_2OH)_3$; $-H_2PO_4^\ominus$; and $-NO_3^\ominus$ and d is an integer from 1 to 10.

2. A composition according to claim 1 wherein said fluorochemical compound has the formula

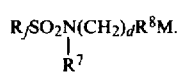

3. A composition according to claim 2 wherein $R_f$ comprises a perfluoroalkyl group containing from about 6 to 12 carbon atoms.

4. A composition in accordance with claim 3 wherein said perfluoroalkyl group contains from about 7 to 8 carbon atoms.

5. A composition in accordance with claim 4 wherein said perfluoroalkyl group contains 8 carbon atoms.

6. A composition according to claim 5 wherein $R^8$ is

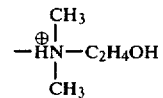

and M is selected from $-H_2PO_4^\ominus$ and $-NO_3^\ominus$.

7. A composition according to claim 6 having the formula

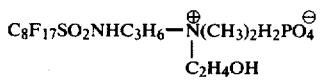

8. A composition according to claim 6 having the formula

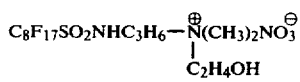

9. A composition according to claim 5 wherein $R^8$ is

and M is selected from hydrogen, sodium, potassium and $-HN(CH_2CH_2OH)_3$.

10. A composition according to claim 9 wherein said fluorochemical compound is

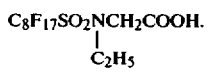

11. A composition according to claim 9 wherein said fluorochemical compound is

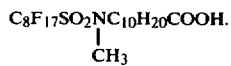

12. A composition according to claim 9 wherein said fluorochemical compound is

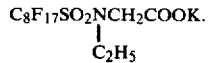

13. A composition according to claim 9 wherein said fluorochemical compound is

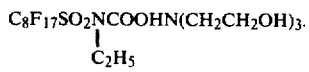

14. A composition according to claim 1 wherein said fluorochemical has the formula

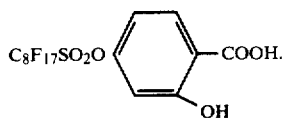

15. A composition according to claim 1 wherein said fluorochemical has the formula

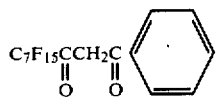

16. The method of inhibiting plaque formation comprising contacting teeth which are substantially free from dental plaque, in an oral environment, with an effective amount of a dentifrice composition comprising at least one ingredient selected from the group consisting of caries prophylactic agents, polishing agents, surfactants, flavoring agents, sweetening agents, thickening agents and humectants, said ingredients being substantially free from polyvalent metal ions, and at least about 0.05% by weight of a fluorochemical compound selected from

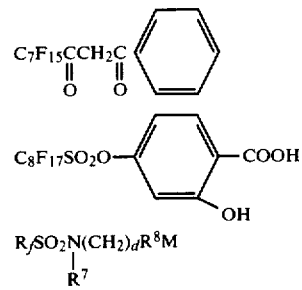

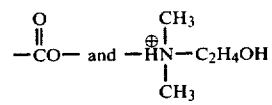

wherein
$R_f$ is a fluorinated, saturated, aliphatic radical having from about 4 to 16 carbon atoms;
$R^7$ is selected from hydrogen, methyl and ethyl;
$R^8$ is selected from $$-\overset{O}{\underset{\|}{C}}O- \quad \text{and} \quad -\overset{CH_3}{\underset{CH_3}{\overset{|}{\overset{\oplus}{H}N}}}-C_2H_4OH$$

M is selected from hydrogen, sodium, potassium, $-HN(CH_2CH_2OH)_3$, $-H_2PO_4^\ominus$ and $-NO_3^\ominus$ and d is an integer from 1 to 10.

* * * * *